United States Patent [19]

Stockinger et al.

[11] Patent Number: 5,070,163

[45] Date of Patent: Dec. 3, 1991

[54] BISMIDES OF ALLYL- OR METHALLYLBICYCLO(2.2.1)HEPT-5-ENE-2,3-DICARBOXYLIC ACID

[75] Inventors: Friedrich Stockinger, Courtepin; Andreas Kramer, Düdingen, both of Switzerland

[73] Assignee: Ciba-Geigy Corporation, Ardsley, N.Y.

[21] Appl. No.: 401,350

[22] Filed: Aug. 31, 1989

[30] Foreign Application Priority Data

Sep. 2, 1988 [CH] Switzerland ............ 3281/88

[51] Int. Cl.$^5$ .................. C08F 26/06; C07D 209/48
[52] U.S. Cl. ...................... 526/259; 548/461
[58] Field of Search ............ 548/461; 526/259

[56] References Cited

U.S. PATENT DOCUMENTS

| | | | |
|---|---|---|---|
| 3,781,240 | 12/1973 | Lubowitz | 260/37 NT |
| 3,781,249 | 12/1973 | Lubowitz | 260/78 TF |
| 4,196,144 | 4/1980 | Darms | 260/571 |
| 4,515,962 | 5/1985 | Renner | 548/435 |
| 4,517,321 | 5/1985 | Gardmer et al. | 523/400 |
| 4,535,170 | 8/1985 | Sonnenberg | 548/462 |
| 4,604,437 | 8/1986 | Renner | 526/262 |
| 4,666,997 | 5/1987 | Renner et al. | 525/502 |
| 4,691,025 | 9/1987 | Domeier et al. | 548/521 |
| 4,769,475 | 9/1988 | Sasaki et al. | 548/462 |
| 4,855,390 | 8/1989 | Sasaki et al. | 528/170 |

FOREIGN PATENT DOCUMENTS

| | | |
|---|---|---|
| 192480 | 8/1986 | European Pat. Off. |
| 979407 | 1/1965 | United Kingdom . |
| 1227387 | 4/1971 | United Kingdom . |

OTHER PUBLICATIONS

PCT WO87/00835.
J. Polym. Sci., A-1(4), pp. 2093-2095.

*Primary Examiner*—Joseph L. Schofer
*Assistant Examiner*—Alex H. Walker
*Attorney, Agent, or Firm*—JoAnn Villamizar

[57] ABSTRACT

Compounds of the formula I

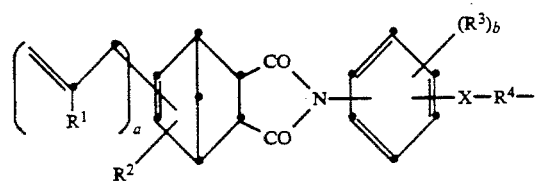

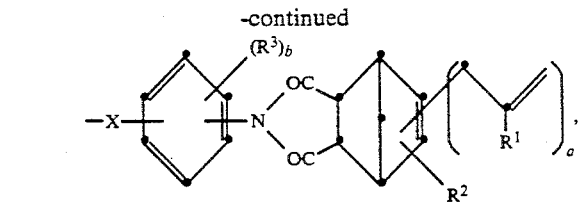

in which a is 1, 2 or 3, b is 0, 1, or 2, $R^1$ and $R^2$, independently of one another are hydrogen or methyl, $R^3$ is $C_1$-$C_6$alkyl, $R^4$ is selected from the group consisting of the formulas IIa, IIb, IIc, IId, IIe or IIf

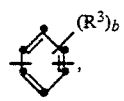 (IIa)

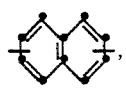

(IIb)

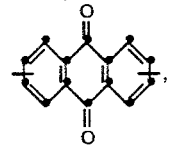

(IIc)

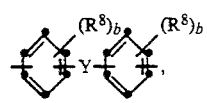

(IId)

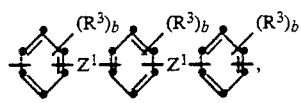

(IIe)

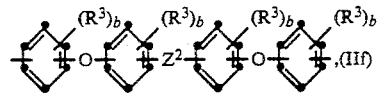

(IIf)

X is —O—, —S—, —CO—, —COO—, —CO—NR$^5$— or —CR$^6$R$^7$—, Z$^1$ is —CR$^6$R$^7$—, Z$^2$ is —SO$_2$— or —CO—, Y is a direct C—C bond, —O—, —S—, —SO—, —SO$_2$—, —CO—, —P(O)R$^9$—, —COO—, —CO—NR$^5$—, —C$_n$H$_{2n}$— or —CR$^{10}$R$^{11}$—, n is an integer from 1 to 12, R$^5$ is hydrogen or C$_1$-C$_6$alkyl, R$^6$ and R$^7$, independently of one another, are hydrogen, or C$_1$-C$_6$alkyl, —CF$_3$, cyclohexyl or phenyl, or R$^6$ and R$^7$ together with the common C atom are a cycloalkylidene radical having 5 to 7 ring carbon atoms, R$^8$ is C$_1$-C$_6$alkyl, chlorine or bromine, R$^9$ is methyl, cyclohexyl or phenyl, R$^{10}$ is —CF$_3$, cyclohexyl or phenyl, R$^{11}$ can adopt one of the meanings of R$^{10}$ or is additionally hydrogen, or R$^{10}$ and R$^{11}$ together with the common C atom are a cycloalkylidene radical having 5 to 7 ring carbon atoms.

The compounds can be used as matrix resin, in particular in combination with polymaleimides, for the production of composite materials.

18 Claims, No Drawings

BISMIDES OF ALLYL- OR METHALLYLBICYCLO(2.2.1)HEPT-5-ENE-2,3-DICARBOXYLIC ACID

The present invention relates to selected bisimides of allyl- or methallyl-bicyclo[2.2.1]hept-5-ene-2,3-dicarboxylic acid, a process for their preparation, selected intermediates, combinations of these bisimides with polymaleimides and the crosslinked products obtainable by curing these bisimides or these combinations.

EP-A 105,024 describes, inter alia, bisimides based on allyl- or methallyl-bicyclo[2.2.1]hept-5-ene-2,3-dicarboxylic acid and alkylenediamines or binuclear carbocyclic-aromatic diamines. The compounds are heat-curable and are suitable, for example, for the preparation of fibre-reinforced plastics.

EP-A 152,372 discloses, inter alia, bisimides based on allyl- or methallyl-methylbicyclo[2.2.1]hept-5-ene-2,3-dicarboxylic anhydride and the abovementioned diamines. These compounds are also suitable for the preparation of matrix resins for composite materials.

Moreover, EP-A 175,648 discloses combinations of the abovementioned bisimide derivatives with polymaleimides. The cured products obtained from these combinations are distinguished by good mechanical properties, such as good bending strength, tensile shear strength or interlaminar shear strength, and also by low embrittlement and high glass transition temperatures.

Bisimides based on allyl- or methallyl-bicyclo[2.2.1]hept-5-ene-2,3-dicarboxylic acid and selected diamines, which can be processed to give thermosets having excellent mechanical properties, such as improved outer fibre stress and bending strength, have now been found. The cured products are furthermore distinguished by low water absorption.

The present invention relates to compounds of the formula I

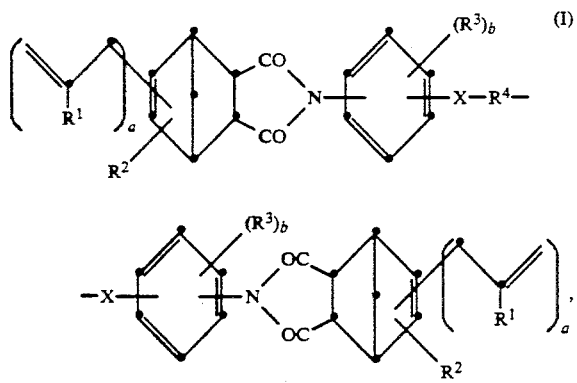

in which a is 1, 2 or 3, b is 0, 1 or 2, $R^1$ and $R^2$, independently of one another, are hydrogen or methyl, $R^3$ is $C_1$-$C_6$alkyl, $R^4$ is selected from the group consisting of the formulas IIa, IIb, IIc, IId, IIe or IIf

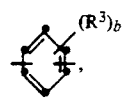

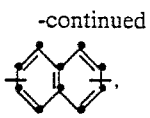

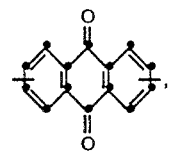

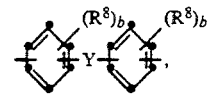

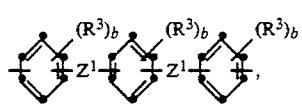

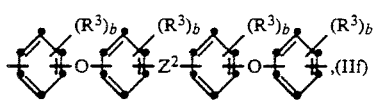

X is —O—, —S—, —CO—, —COO—, —CO—NR$^5$— or —CR$^6$R$^7$—, $Z^1$ is —CR$^6$R$^7$—, $Z^2$ is —SO$_2$— or —CO—, Y is a direct C—C bond, —O—, —S—, —SO—, —SO$_2$—, —CO—, —P(O)R$^9$—, —COO—, —CO—NR$^5$—, —C$_n$H$_{2n}$— or —CR$^{10}$R$^{11}$—, n is an integer from 1 to 12, $R^5$ is hydrogen or $C_1$-$C_6$alkyl, $R^6$ and $R^7$, independently of one another, are hydrogen, $C_1$-$C_6$alkyl, —CF$_3$, cyclohexyl or phenyl, or $R^6$ and $R^7$ together with the common C atom are a cycloalkylidene radical having 5 to 7 ring carbon atoms, $R^8$ is $C_1$-$C_6$alkyl, chlorine or bromine, $R^9$ is methyl, cyclohexyl or phenyl, $R^{10}$ is —CF$_3$, cyclohexyl or phenyl, $R^{11}$ can adopt one of the meanings of $R^{10}$ or is additionally hydrogen, or $R^{10}$ and $R^{11}$ together with the common C atom are a cycloalkylidene radical having 5 to 7 ring carbon atoms.

The indices a and b and the radicals $R^1$, $R^2$, $R^3$, $R^5$ to $R^{11}$ in a molecule of the formula I can each have different meanings within the definitions given.

Any $C_1$-$C_6$alkyl radicals can be branched or preferably straight-chain alkyl radicals.

Examples of these are methyl, ethyl, n-propyl, isopropyl, n-butyl, sec-butyl, tert-butyl, n-pentyl, n-hexyl or 1-ethylbutyl. Methyl is preferred.

Examples of cycloalkylidene radicals are cyclopentylidene, cycloheptylidene and in particular cyclohexylidene.

The index a is preferably 1. The index b is preferably 0.

The index n is preferably 1 to 6.

$R^2$ is preferably hydrogen and $R^3$ and $R^8$ are preferably methyl.

$R^5$ is preferably methyl and in particular hydrogen.

The radical $R^4$ is preferably selected from a group of the formulae IIa, IIb or IId, as defined above.

X is preferably —CR$^6$R$^7$— or in particular —O—.

The bridge member Y is preferably a direct C—C bond, —S—, —SO$_2$—, —CH$_2$—, —C(CH$_3$)$_2$— or —CO—, and in particular —C(CF$_3$)$_2$— and —O—.

The bridge member $Z^1$ is preferably —CH$_2$— or in particular —C(CH$_3$)$_2$—.

Preferred radicals $R^6$ and $R^7$ are hydrogen, $C_1$-$C_6$alkyl and —$CF_3$; hydrogen, methyl or —$CF_3$ are very particularly preferred.

Compounds of the formula I in which a is 1, b is 0 and $R^2$ is hydrogen are preferred.

Furthermore, compounds of the formula I in which $R^4$ is selected from a group of the formulas IIa, IIb or IId and b is 0 are preferred.

Compounds of the formula I in which X is —$C(CH_3)_2$— or in particular —O— are particularly preferred.

In further preferred compounds of the formula I, Y is a direct C—C bond, —S—, —$SO_2$—, —$CH_2$—, —$C(CH_3)_2$—, —CO— or in particular —O— or —$C(CF_3)_2$— and Z is —$CH_2$— or —$C(CH_3)_2$—.

Compounds of the formula I in which X is —$C(CH_3)_2$— or in particular —O— and $R^4$ is a group of the formulae IIg, IIh or IIi

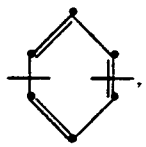

(IIg)

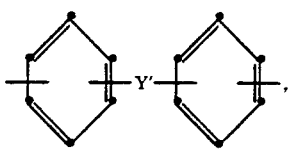

(IIh)

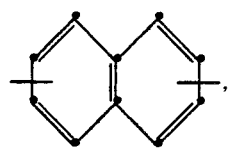

(IIi)

in which Y' is a direct C—C bond, —O—, —S—, —$SO_2$—, —$C(CF_3)_2$— or —$C_nH_{2n}$—, n is as defined above, the free valencies are in the 1,2- or 1,4-position with respect to one another in radical IIg, in the 1,2- or 1,4-position with respect to the corresponding bridge in radical IIh and in the 1,5-, 2,6- or 2,7-position with respect to one another in radical IIi are very particularly preferred.

In further very particularly preferred compounds of the formula I, X is —O— and $R^4$ is a radical of the formula IIj

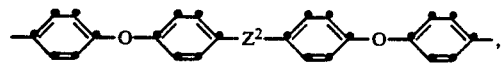

(IIj)

in which $Z^2$ is as defined above.

Compounds of the formula III

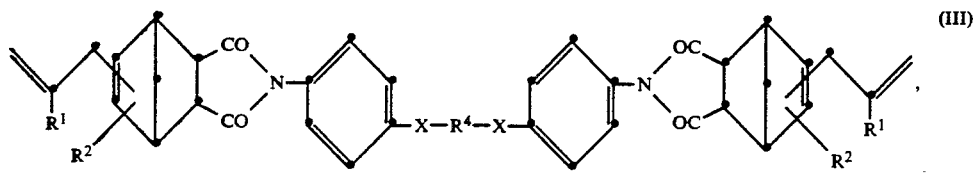

(III)

in which $R^1$, $R^2$, $R^4$ and X are as defined above are particularly preferred.

The compound of the formula IIIa

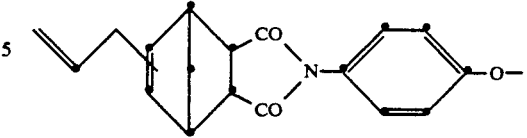

(IIIa)

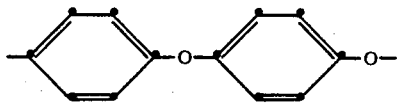

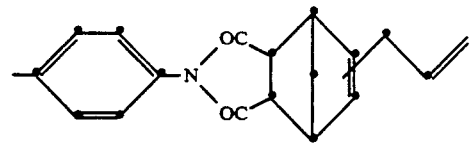

is very particularly preferred.

The bisimides according to the invention can be prepared in analogy to known processes by reaction of an anhydride of the formula IVa

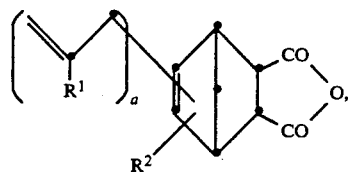

(IVa)

at elevated temperature, while distilling off the water formed in the reaction, with a diamine of the formula V

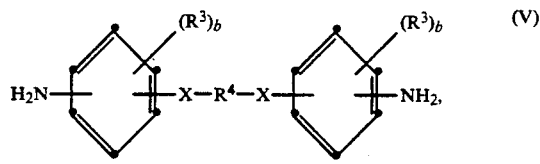

(V)

in which $R^1$, $R^2$, $R^3$, $R^4$, X, a and b are as defined above.

The diamines of the formula V are advantageously used in a stoichiometric ratio. The reaction can be carried out without a solvent or preferably in the presence of an inert organic solvent which can be used for the azeotropic removal of the water (entrainer). Examples of suitable solvents are aromatic hydrocarbons, such as toluene, xylene or mesitylene, or halogenated aromatic hydrocarbons, such as chlorobenzene or dichlorobenzene.

The reaction is usually carried out at temperatures between 110° and 200° C. The reaction time is dependent on the rate of the elimination of water and is usually about 2 to 20 hours.

The anhydrides of the formula IV can be prepared in accordance with the process described in U.S. Pat. No. 3,105,839 by reacting sodium cyclopentadienide or sodium methylcyclopentadienide with an allyl or methallyl halide, preferably an allyl or methallyl chloride, followed by a Diels-Alder reaction with maleic anhydride.

Anhydrides of the formula IV which contain several allyl or methallyl groups can be obtained in analogy to the above process by reaction with a stoichiometric excess of allyl or methallyl halide. Although U.S. Pat. No. 3,105,839 states that the (meth)allyl group is bound to the 7-position of the bicyclic system, more recent investigations show that an isomeric mixture with respect to the position of the allyl or methallyl group and also the endo and exo configuration of the anhydride moiety is formed.

Some of the bisimides according to the invention in which X is —O—, $R^4$ is a radical of the formula IId and Y is —CO— or —$SO_2$— can also be prepared by reaction of essentially two equivalents of a phenol of the formula IVb with a dibromide, dichloride or difluoride of the formula IVc in the presence of a base, such as $K_2CO_3$, at elevated temperature

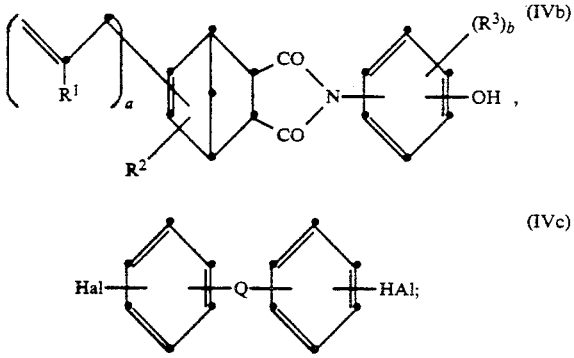

In these formulae, $R^1$, $R^2$, $R^3$, a and b are as defined above, Hal is F, Cl or Br and Q is —CO— or —$SO_2$—.

The reaction is advantageously carried out in an inert organic solvent at elevated temperatures. Examples of these are listed above.

The compounds of the formula IVb are disclosed, for example, in EP-A 166,693. The compounds of the formula IVc are also known per se and in part commercially available.

The diamines of the formula V are in part known or can be prepared by analogy to known diamines.

Thus, the compounds of the formula Va

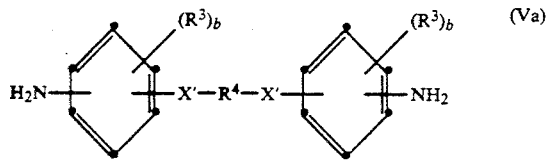

in which X' is —S— or —O— and $R^3$, $R^4$ and b are as defined above can be prepared, for example, by reacting a bisphenol HX'—$R^4$—X'H in the presence of a base, for example $K_2CO_3$, with a chloro- or bromonitrobenzene and hydrogenating the dinitro compound with hydrogen in the presence of a hydrogenation catalyst known per se, such as Pd/carbon, Raney nickel or Fe/HCl, to give the corresponding diamine.

The compounds of the formula Va in which X' is —COO— can be obtained directly, for example, by esterification of a dicarboxylic acid HOOC—$R^4$—COOH or one of its ester-forming derivatives, such as the acid chloride, with an aminophenol; or the preparation is carried out by reaction of a nitrophenol with a dicarboxylic acid HOOC—$R^4$—COOH or one of its ester-forming derivatives, followed by hydrogenation to the diamine.

The compounds of the formula Va in which X' is —COO— can also be prepared by reaction of a nitrobenzoyl chloride with a bisphenol HO—$R^4$—OH, followed by reduction to the diamine.

The compounds of the formula Va in which X' is —CO—$NR^5$— can be obtained, for example, by reaction of a diamine $HR^5N$—$R^4$—$NR^5H$ with a nitrobenzoyl chloride, followed by hydrogenation of the dinitro compound to the diamine. Examples of these reactions can be found in J. Polymer Sci.: Part A-1, 4(9), 2093-2105 (1966) or GB-A 979,407.

The compounds of the formula Va in which X' is —CO—$NR^5$— can also be obtained by reacting a dicarboxylic acid HOOC—$R^4$—COOH or one of its amide-forming derivatives, such as the ester or the acid chloride, with a nitroaniline, followed by reduction of the dinitro compound to the diamine. Examples of these reactions can be found in GB-A 1,227,387.

The compounds of the formula Va in which X' is —CO— can be obtained, for example, by reaction of a nitrobenzoyl chloride with an aromatic compound H—$R^4$—H in the presence of $AlCl_3$, followed by hydrogenation of the dinitro compound to the diamine.

The compounds of the formula Va in which X' is —$CR^6R^7$— can be obtained by condensation of an aromatic compound H—$R^4$—H with an aldehyde or ketone $R^6$—CO—$R^7$ and an aminobenzene in alkaline medium in a manner known per se.

These reactions are advantageously carried out in the presence of an inert organic solvent. Examples of these are aprotic polar solvents, such as dimethylformamide (DMF), dimethylacetamide (DMA), N-methylpyrrolidone (NMP), dimethyl sulfoxide (DMSO) or cyclic ureas, such as tetramethyleneurea.

The reactions are carried out, depending on the reactivity of the starting materials used, in general at 100° to 200° C. The reaction time is usually 2 to 20 hours.

The starting compounds for the preparation of the diamines of the formula V are known per se.

The diamines of the formula V are known in part, for example from U.S. Pat. No. 4,517,321 or from U.S. Pat. No. 4,196,144.

The novel diamines of the formulae VIa, VIb, VIc and VId are also provided by the present invention

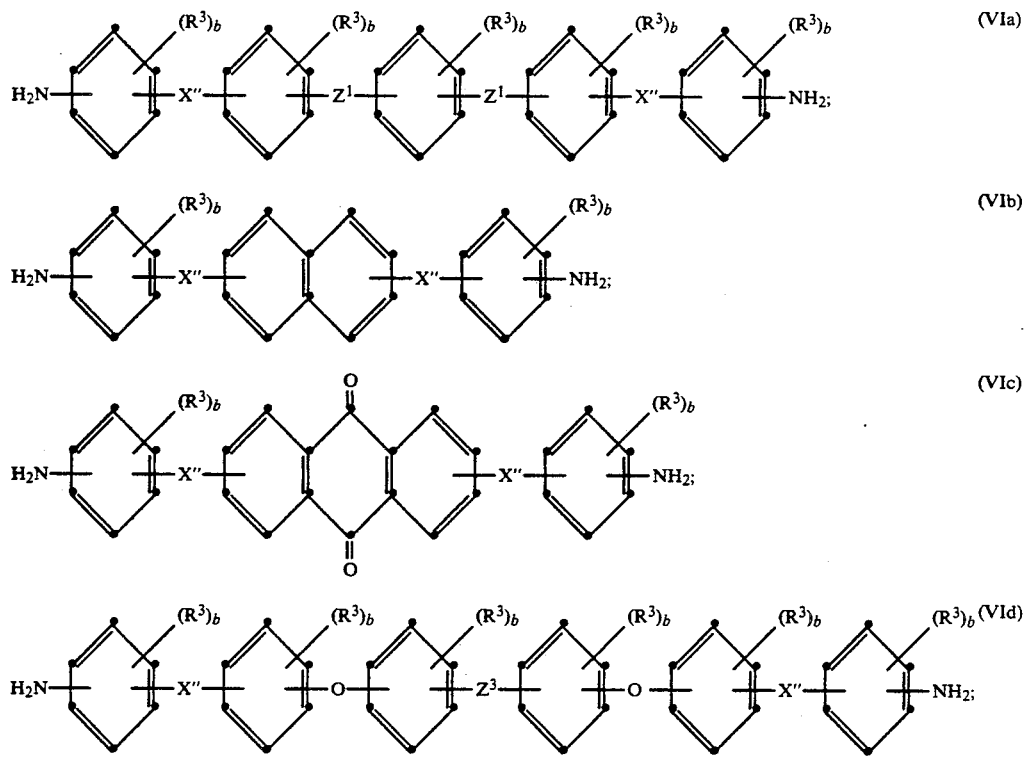
In these formulae, $R^3$, $Z^1$ and b are as defined above, $X''$ is —O—, —S—, —CO— or —COO— and $Z^3$ is —CO—.
The invention further relates to the dinitro intermediates of the formulae VIIa, VIIb, VIIc and VIId, which can be prepared in the manner described above and can be used as starting materials for the preparation of selected diamines of the formulae VIa, VIb, VIc and VId
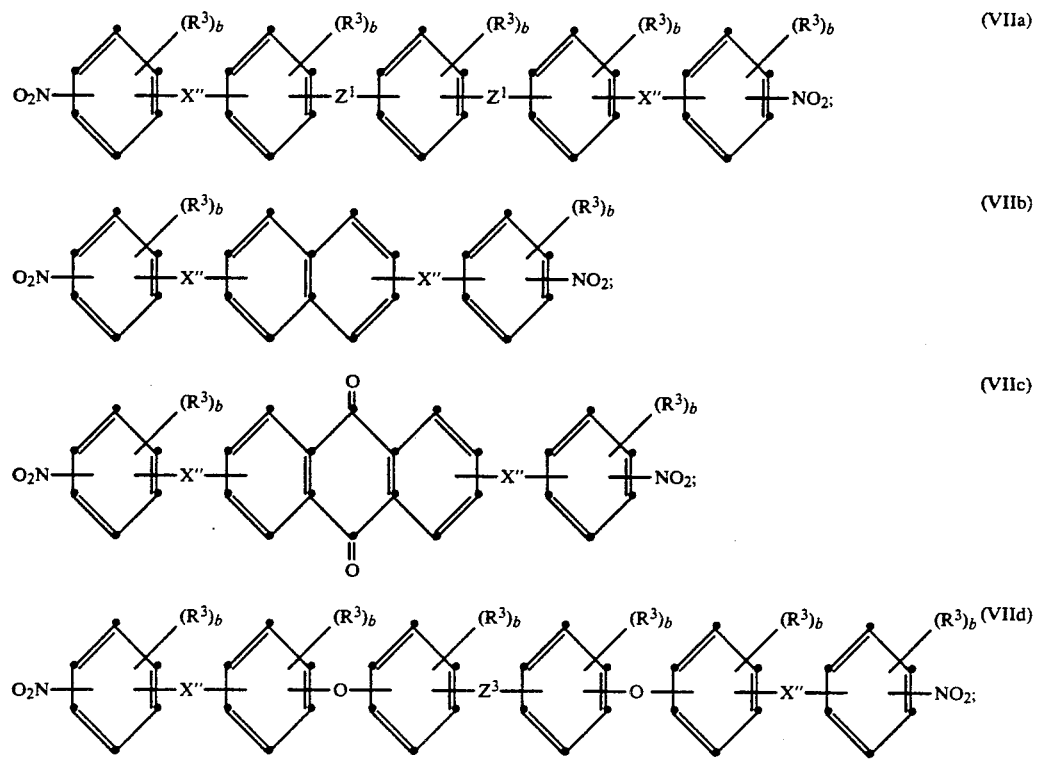

In these formulae, $R^3$, $Z^1$, b and $X''$ are as defined above and $Z^3$ is —CO—.

The compounds of the formula I are liquid or low-melting solid substances which can be polymerized to solid products having high glass transition temperatures and heat- and water-resistance.

These products can be used in many ways, for example as laminating or electrical insulating resins, as high-temperature adhesives or for the production of coatings or mouldings, such as prepregs or composite materials.

Preferably, the compounds of the formula I are used in combination with compounds of the formulae VIII or IX listed below. These mixtures are distinguished by a high reactivity. Mouldings and composite materials consisting of the compounds of the formula I and polymaleimides are distinguished in particular by good mechanical properties, such as low outer fibre stress and high interlaminar shear strength, and by high glass transition temperatures. Furthermore, the stability of cured resins of this type to thermal oxidation is surprisingly good.

The invention accordingly also relates to compositions containing

A) at least one compound of the formula I and

B) at least one compound of the formulae VIII or IX

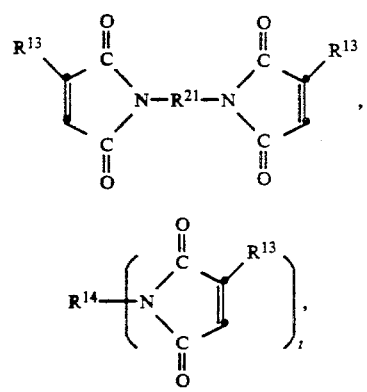

(VIII)

(IX)

in which t is an integer from 3 to 12, $R^{12}$ is alkylene, cycloalkylene, arylene, aralkylene or a divalent heterocyclic radical containing one or two N, O or S atoms, $R^{13}$ is methyl and in particular hydrogen and $R^{14}$ is a t-valent radical of an aromatic polyamine after the removal of t amino groups.

The molar ratio of component A) to component B) is in general about 1:0.1 to about 1:1, preferably about 1:1.

Mixtures of compounds of the formula I or of formulae VIII and IX can also be used.

Alkylene radicals $R^{12}$ are usually straight-chain alkylene radicals. $C_2-C_{12}$alkylene radicals are preferred.

Examples of alkylene radicals are ethylene, tri-, tetra-, penta-, hexa-, hepta-, octa-, nona-, deca-, undeca-, dodeca-, tetradeca-, hexadeca-, octadeca- or eicosa-methylene or the radical of trimethylhexamethylenediamine.

Cycloalkylene $R^{12}$ is usually cyclopentylene, cyclohexylene, cycloheptylene, cyclooctylene or cyclododecylene. Cyclohexylene is preferred. However, these radicals can also be alkyl-substituted cycloalkylene radicals or the cycloalkylene radicals are part of an aliphatic chain. An example of this is the radical of isophoronediamine.

Arylene radicals $R^{12}$ are usually mono- to tetranuclear carbocyclicaromatic radicals, which may carry one or more inert substituents, such as alkyl or alkoxy. Multinuclear radicals can be fused or linked to one another via a bridging group, for example as defined above for Y.

Preferred radicals $R^{12}$ of this type are the radicals of the formulae IIa to IIf defined above, in particular the radicals of the formulae IIa or IId.

Examples of these radicals are 1,3- or 1,4-phenylene, toluylidene or diphenylmethane-4,4'-diyl, 4,4'-oxydiphenylene, 4,4'-sulfonyldiphenylene or 4,4'-biphenylene.

An example of aralkylene is xylylene.

Divalent heterocyclic radicals $R^{12}$ which contain one or two N, O or S atoms are usually five- or six-membered nonaromatic or in particular aromatic radicals preferably consisting of one or two heterocyclic systems linked via a bridging group, for example as defined above for Y.

Five-membered mononuclear aromatic groups having one O or S atom in the ring, such as furandiyl or thiophenediyl, or six-membered nonaromatic N-heterocyclic radicals, such as pyrazolidinediyl, piperazinediyl, morpholinediyl or hydantoindiyl, are preferred.

$R^{14}$ is preferably a radical of the formula X

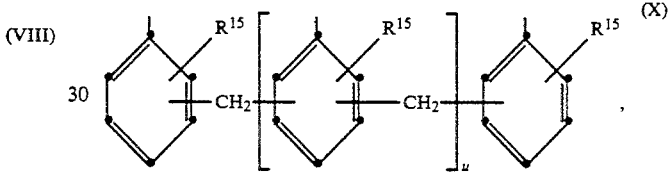

(X)

in which u is 1 to 4 and $R^{15}$ is hydrogen or methyl.

Preferred compositions according to the invention contain, as component A), a compound of the formula I in which a is 1, b is 0, X is —O— and $R^4$ is a radical of the formula IId in which Y is —O— and, as component B), a compound of the formula VIII in which $R^{13}$ is hydrogen and $R^{12}$ is a binuclear aromatic radical whose nuclei are linked via a bridging group, in particular a radical of the formula IId. Particularly preferred compositions according to the invention contain a combination of a compound of the formula IIIa with 4,4'-diphenylmethanebismaleimide, preferably in a molar ratio of about 1:1.

The compounds of the formulae VIII or IX are known per se and described, for example, in EP-A 175,648.

The invention accordingly also relates to the use of the compounds of the formula I according to the invention or the compositions containing components A) and B) defined above for the production of mouldings, coatings or bonded joints.

The compounds according to the invention or compositions which contain components A) and B) can be used directly and can be polymerized, or they can first be dissolved in an inert organic solvent, such as DMF, DMA, NMP, toluene, xylene, methyl ethyl ketone, ethylene glycol monoalkyl and dialkyl ethers which have 1-4 C atoms in the alkyl groups or a similar solvent customary in the coating industry.

These solutions can serve as impregnating agents or as coating agents or even as an article for despatch to the consumer.

The compounds of the formula I or compositions which contain components A) and B) can be converted into novel polymers which are distinguished by the advantageous properties mentioned above.

Thus the invention also relates to the cured products obtainable by heating the compouds of the formula I or the compositions which contain components A) and B).

The compounds of the formula I are polymerized by heating them advantageously to temperatures between 180° and 300° C., in particular between 200° and 250° C. Depending on the temperature, the duration of the polymerization is advantageously between 6 and 60 hours.

The compositions which contain components A) and B) are polymerized by heating them advantageously to temperatures between 150° and 300° C., in particular between 180° and 250° C.

Curing catalysts can also be added to the compounds of the formula I or the compositions which contain components A) and B), for example organic peroxides, such as di-tert-butyl peroxide, dicumyl peroxide or tert-butyl perbenzoate; or Lewis acids, such as $FeCl_3$, $ZnCl_2$, $BCl_3$, $BF_3$, $AlCl_3$, $TiCl_4$, $SnCl_4$ or $SbCl_5$.

It is of course also possible to add inert and stable additives, such as fillers, reinforcing agents, in particular glass fibres, carbon fibres or Aramid fibres, plasticizers, pigments, dyes, mould release agents, flame retardants and other conventional additives to the bisimides of the formula I or the compositions which contain components A) and B) before the polymerization.

The examples which follow illustrate the invention:

A. PREPARATION OF THE BISIMIDES OF THE FORMULA I

EXAMPLE A1

2,2-Bis[4-(4-allyl-bicyclo[2.2.1]hept-5-ene-2,3-dicarboximidylphenoxy)phenyl]hexafluoropropane

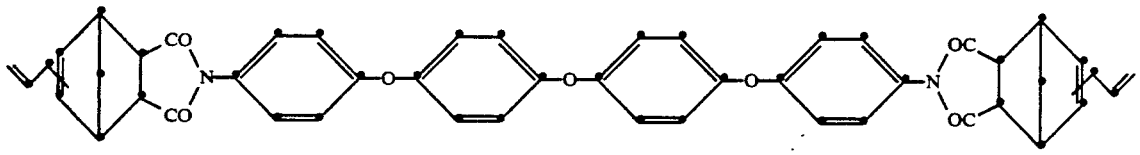

259.2 g (0.5 mol) of 2,2-bis[4-(4-aminophenoxy)-phenyl]hexafluoropropane and 204.2 g (1.0 mol) of allylbicyclo[2.2.1]hept-5-ene-2,3-dicarboxylic anhydride, prepared according to U.S. Pat. No. 3,105,839, in 1200 ml of xylene are reacted at 90° to 136° C. for 6 hours and 40 minutes in a 6 l sulfonating flask equipped with thermometer, blade stirrer, azeotropic distillation head and intensive cooler, and the water of reaction formed is continuously removed by azeotropic distillation. After the reaction is completed, the solution is concentrated at 80° to 95° C. under a waterpump vacuum and then dried at 120° to 160° C./0.2 mbar, until the weight remains constant. This gives 433.1 g (97.2% of theory) of a glassy red-brown bisallylnadicimide having the following analytical data:

|  | Elemental analysis: | | | |
|---|---|---|---|---|
|  | % C | % H | % N | % F |
| calculated: | 68.76 | 4.53 | 3.14 | 12.80 |
| found: | 68.57 | 4.66 | 3.32 | 12.90. |

Molecular weight (by vapour pressure osmosis): 891.
Viscosity (at 150° C.): 5840 mPas.

EXAMPLE A2

4,4'-Bis(4-allylbicyclo[2.2.1]hept-5-ene-2,3-dicarboximidylphenoxy)diphenyl ether

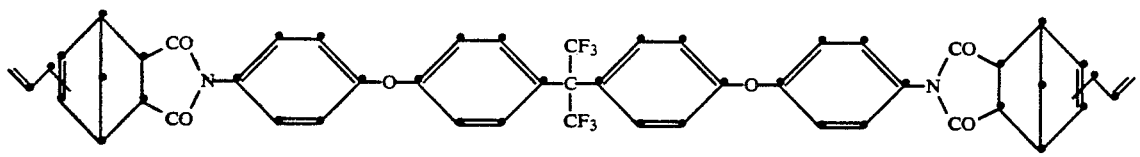

Analogously to Example A1, 576.7 g (1.5 mol) of 4,4'-bis(4'-aminophenoxy)diphenyl ether and 612.7 g (3.0 mol) of allylbicyclo[2.2.1]-hept-5-ene-2,3-dicarboxylic anhydride in 3000 ml of xylene are reacted for 9 hours and 30 minutes and subsequently worked up according to Example A1. This gives 1106 g (97.4% of theory) of a brown glassy product whose viscosity (at 150° C.) is 2560 mPas.

|  | Elemental analysis: | | |
|---|---|---|---|
|  | % C | % H | % N |
| calculated: | 76.17 | 5.33 | 3.70 |
| found: | 75.69 | 5.40 | 3.50. |

Absorption of hydrogen: 5.29 mmol of $H_2$/g (calculated), 4.6 mmol $H_2$/g (found).

Molecular weight (GPC): $M_n=779$; $M_w=913$.

EXAMPLE A3

4,4'-Bis(4-allylbicyclo[2.2.1]hept-5-ene-2,3-dicarboximidylphenoxy)-diphenyl sulfide

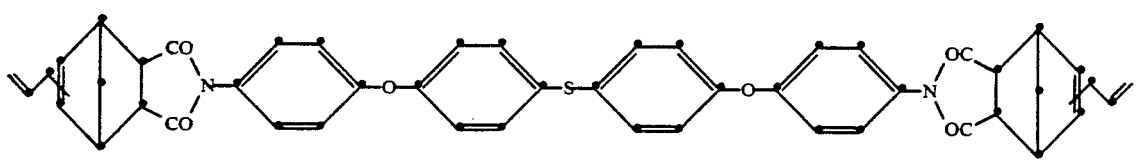

200.25 g (0.5 mol) of 4,4'-bis-(4-aminophenoxy)diphenyl sulfide and 204.2 g (1.0 mol) of allylbicyclo[2.2.1-]hept-5-ene-2,3-dicarboxylic anhydride in 1150 ml of xylene are reacted at 130°-135° C. for 6 hours and 20 minutes and worked up as described in Example A1. This gives 386.1 g (99.9% of theory) of the desired product which has the following analytical data:

|  | Elemental analysis: | | | |
|---|---|---|---|---|
|  | % C | % H | % N | % S |
| calculated | 74.59 | 5.22 | 3.62 | 4.15 |
| found | 74.35 | 5.28 | 3.44 | 4.26. |

Molecular weight (GPC): $M_n=794$; $M_w=842$.
Viscosity (at 150° C.): 940 mPas.

EXAMPLE A4

4,4'-Bis(4-allylbicyclo[2.2.1]hept-5-ene-2,3-dicarboximidylphenoxy)diphenylmethane

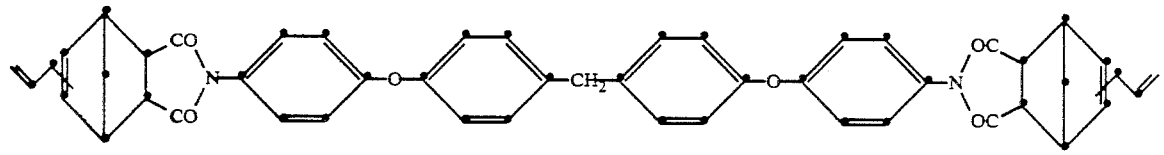

As described in Example A1, 95.6 g (0.25 mol) of

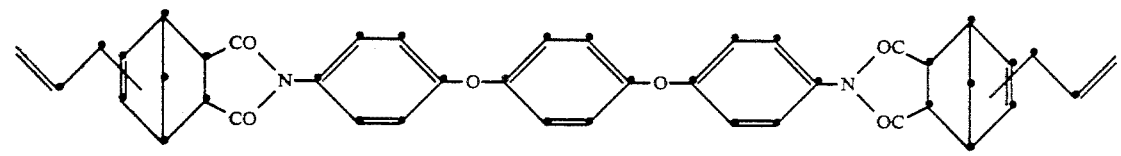

4,4'-bis(4-aminophenoxy)-diphenylmethane and 102.1 g (0.5 mol) of allyl-bicyclo[2.2.1]hept-5-ene-2,3-dicarboxylic anhydride in 600 ml of xylene are reacted at 128°-136° C. for 4 hours and 5 minutes, and the product is isolated analogously to Example A1. This gives 186.9 g (99% of theory) of a brownish glassy bisallylnadicimide.

|  | Elemental analysis: | | |
|---|---|---|---|
|  | % C | % H | % N |
| calculated | 77.96 | 5.61 | 3.71 |
| found | 77.44 | 5.79 | 3.55. |

Absorption of hydrogen: 5.30 mmol of $H_2$/g (calculated), 4.70 mmol of $H_2$/g (found).
Viscosity (at 150° C.): 920 mPas.

EXAMPLE A5

1,3-Bis(4-allylbicyclo[2.2.1]hept-5-ene-2,3-dicarboximidylphenoxy)-benzene

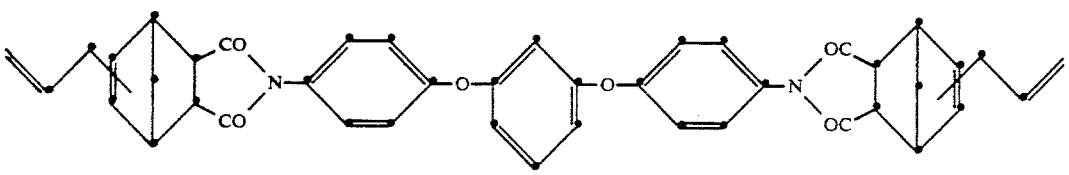

435 g (1.488 mol) of 1,3-bis(4-aminophenoxy)benzene and 607.7 g (2.976 mol) of allylbicyclo[2.2.1]hept-5-ene-2,3-dicarboxylic anhydride in 3420 ml of xylene are reacted according to Example A1 and worked up analogously. This gives 988.6 g (99.9% of theory) of a brownish glassy product whose viscosity (at 150° C.) is 700 mPas.

|  | Elemental analysis: | | |
|---|---|---|---|
|  | % C | % H | % N |
| calculated | 75.89 | 5.46 | 4.21 |
| found | 75.29 | 5.49 | 4.12. |

Absorption of hydrogen: 6.02 mmol of $H_2$/g (calculated), 5.2 mmol of $H_2$/g (found).
Molecular weight (by vapour pressure osmosis): 866.

EXAMPLE A6

1,4-Bis(4-allylbicyclo[2.2.1]hept-5-ene-2,3-dicarboximidylphenoxy)benzene

As described in Example A1, 146.1 g (0.5 mol) of 1,4-bis(4-aminophenoxy)-benzene and 204.2 g (1.0 mol) of allylbicyclo[2.2.1]hept-5-ene-2,3-dicarboxylic anhydride in 1150 ml of xylene are reacted and worked up. This gives 332 g (99.9% of theory) of the desired bisallylnadicimide which has a viscosity (at 150° C.) of 1080 mPas.

|  | Elemental analysis: | | |
|---|---|---|---|
|  | % C | % H | % N |
| calculated | 75.89 | 5.46 | 4.21 |
| found: | 75.79 | 5.55 | 4.10. |

Absorption of hydrogen: 6.02 mmol of $H_2$/g (calculated), 5.3 mmol of $H_2$/g (found).

EXAMPLE A7

1,3-Bis[1-(4-allylbicyclo[2.2.1]hept-5-ene-2,3-dicarboximidylphenyl)-1-methylethylidene]benzene

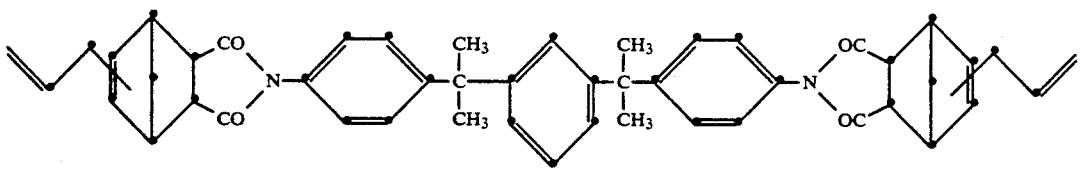

68.9 g (0.2 mol) of an industrially prepared 1,3-bis[1-(4-aminophenyl)-1-methylethylidene]benzene and 81.7 g (0.4 mol) of allylbicyclo[2.2.1]-hept-5-ene-2,3-dicarboxylic anhydride in 450 ml of xylene are reacted and isolated analogously to Example A1. This gives a brownish glassy bisimide whose softening point is 86° C.

| Elemental analysis: | | | |
|---|---|---|---|
| | % C | % H | % N |
| calculated: | 79.97 | 6.26 | 3.11 |
| found: | 79.55 | 6.22 | 3.07. |

Absorption of hydrogen: 4.44 mmol of $H_2$/g (calculated), 4.0 mmol of $H_2$/g (found).

EXAMPLE A8

1,4-Bis-{1-[4-(4-allylbicyclo[2.2.1]hept-5-ene-2,3-dicarboximidylphenoxy)phenyl]-1-methylethylidene}benzene

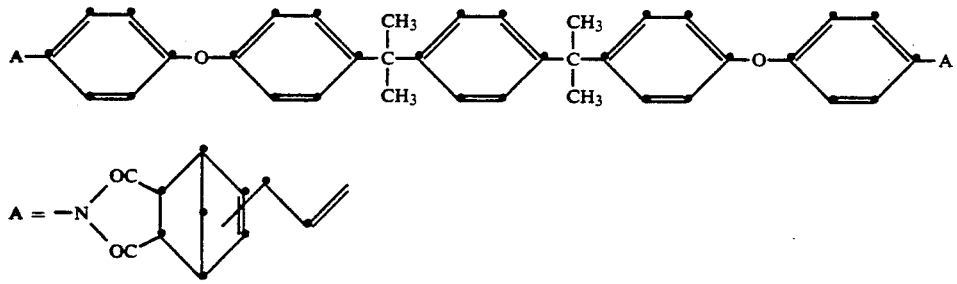

According to Example A1, 292.2 g (0.5 mol) of 1,4-bis-{1-[4-(4-aminophenoxy)phenyl]-1-methylethylidene}benzene and 204.2 g (1.0 mol) of allylbicyclo[2.2.1]hept-5-ene-2,3-dicarboxylic anhydride in 1200 ml of xylene are reacted and worked up. This gives 448.9 g (99.6% of theory) of the desired bisimide whose viscosity (at 150° C.) is 5440 mPas.

| Elemental analysis: | | | |
|---|---|---|---|
| | % C | % H | % N |
| calculated: | 80.42 | 6.75 | 3.91 |
| found: | 79.95 | 6.83 | 3.62. |

Absorption of hydrogen: 5.58 mmol of $H_2$/g (calculated), 5.1 mmol of $H_2$/g (found).

EXAMPLE A9

2,2'-Bis(4-allylbicyclo[2.2.1]hept-5-ene-2,3-dicarboximidylphenoxy)biphenyl

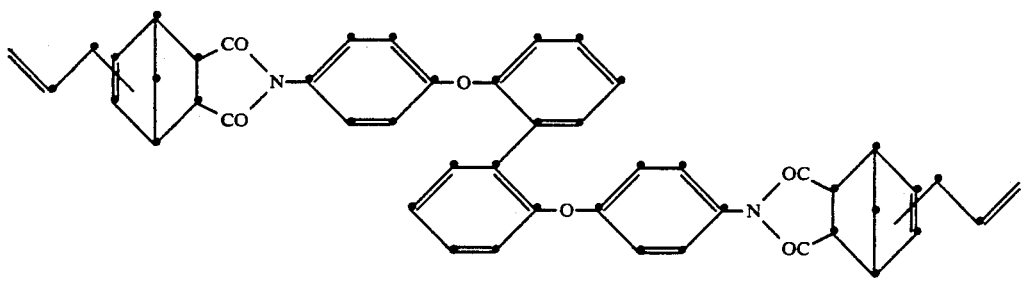

408 g (2 mol) of allylbicyclo[2.2.1]hept-5-ene-2,3-dicarboxylic anhydride and 368 g (1 mol) of 2,2'-bis(4-aminophenoxy)biphenyl are initially introduced in 2000 ml of toluene and heated under reflux for 16 hours in a water separator. The mixture is then worked up as described in Example A1. This gives 728 g (98% of theory) of a red-brown resin which is solid at room temperature and has a softening point of 78° C.

| Elemental analysis: | | | |
|---|---|---|---|
| | % C | % H | % N |
| calculated: | 77.82 | 5.44 | 3.78 |
| found: | 77.58 | 5.57 | 3.65. |

Molecular weight (GPC): $M_n = 563$; $M_w = 576$.

EXAMPLE A10

2,2-Bis-{4-(4-allylbicyclo[2.2.1]hept-5-ene-2,3-dicarbox-imidylphenoxy)phenyl}propane

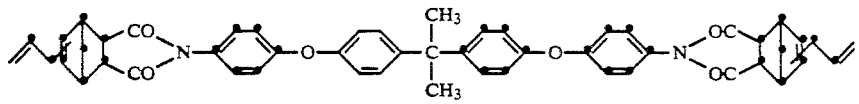

61.5 g (0.15 mol) of 2,2-bis-{4-(4-aminophenoxy)-phenyl}propane and 61.2 g (0.3 mol) of allylbicyclo[2.2.1]hept-5-ene-2,3-dicarboxylic anhydride in 400 ml of xylene are reacted according to Example A1 at 109°–131° C. for 5 hours and 35 minutes and worked up analogously. This gives 116.2 g (99% of theory) of a brown glassy resin whose viscosity (at 180° C.) is 430 mPas.

| | Elemental analysis: | | |
|---|---|---|---|
| | % C | % H | % N |
| calculated: | 78.24 | 5.92 | 3.58 |
| found: | 78.00 | 6.07 | 3.44. |

Molecular weight (GPC): $M_n = 779$; $M_w = 796$.

Absorption of hydrogen: 5.11 mmol of $H_2/g$ (calculated); 4.8 mmol of $H_2/g$ (found).

EXAMPLE A11

4,4'-Bis(4-allylbicyclo[2.2.1]hept-5-ene-2,3-dicarbox-imidylphenoxy)biphenyl

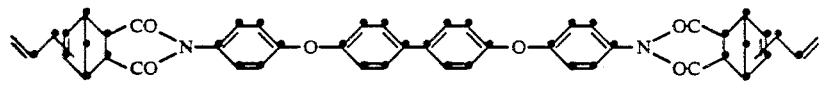

Analogously to Example A1, 110.5 g (0.3 mol) of 4,4'-bis(4-aminophenoxy)-biphenyl and 122.5 g (0.6 mol) of allylbicyclo[2.2.1]hept-5-ene-2,3-dicarboxylic anhydride in 200 ml of xylene are reacted at 129°–136° C. for 17 hours and worked up as described in Example A1. This gives 219.1 g (98.6% of theory) of a brown solid bisimide whose viscosity (at 180° C.) is 1140 mPas.

| | Elemental analysis: | | |
|---|---|---|---|
| | % C | % H | % N |
| calculated | 77.82 | 5.44 | 3.78 |
| found | 77.07 | 5.49 | 3.63. |

EXAMPLE A12

4,4'-Bis(4-allylbicyclo[2.2.1]hept-5-ene-2,3-dicarbox-imidylphenoxy)diphenyl sulfone

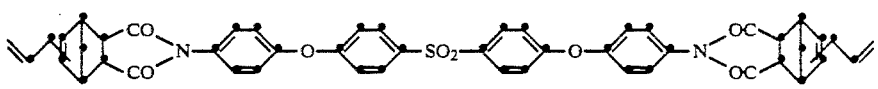

129.8 g (0.3 mol) of 4,4'-bis(4-aminophenoxy)diphenyl sulfone and 122.5 g (0.6 mol) of allylbicyclo[2.2.1]hept-5-ene-2,3-dicarboxylic anhydride in 200 ml of xylene are reacted at 119°–137° C. for 18 hours and 40 minutes and worked up analogously to Example A1. This gives 237.2 g (98.2% of theory) of the desired bisimide whose viscosity (at 180° C.) is 5860 mPas.

| | Elemental analysis: | | | |
|---|---|---|---|---|
| | % C | % H | % N | % S |
| calculated | 71.63 | 5.01 | 3.48 | 3.98 |
| found: | 70.67 | 5.11 | 3.61 | 3.90. |

Molecular weight (GPC): $M_n = 832$; $M_w = 898$.

EXAMPLE A13

4,4'-Bis((4-allylbicyclo[2.2.1]hept-5-ene-2,3-dicarbox-imidylphenoxy)phenoxy)diphenyl sulfone

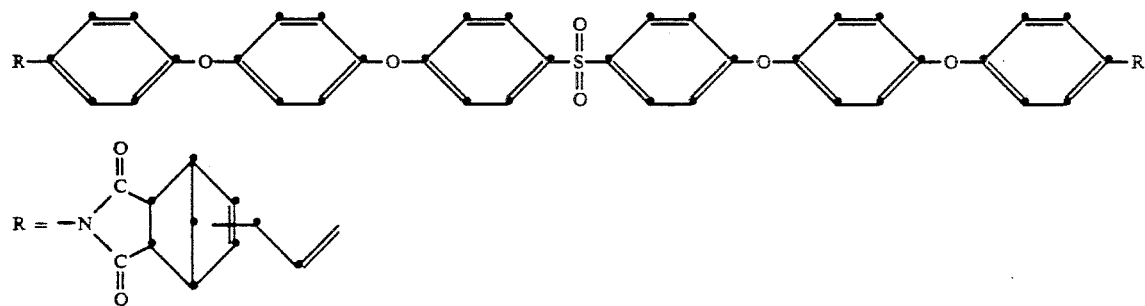

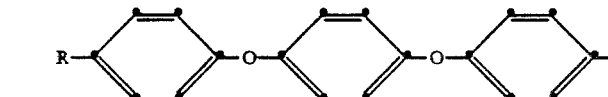

8.0 g (0.0129 mol) of bis(4-(4-aminophenoxy)phenoxy)diphenyl sulfone and 5.27 g (0.0258 mol) of allylbicyclo[2.2.1]hept-5-ene-2,3-dicarboxylic anhydride in 30 ml of xylene and 30 ml of dimethylacetamide are reacted according to Example A1 at 143° C.–152° C. for 19 hours and 40 minutes, and the water of reaction formed is removed continuously by azeotropic distillation.

The mixture is worked up analogously to Example A1 to give 11.3 g (88.3% of theory) of a glassy solid imide whose viscosity at 180° C. is 2440 mPas.

| | Elemental analysis: | | |
|---|---|---|---|
| | % C | % H | % N |
| calculated | 72.86 | 4.89 | 2.83 |
| found | 72.45 | 5.23 | 2.95. |

B. WORKING EXAMPLES

EXAMPLE B1

A bisallylnadicimide prepared according to Synthesis Example A2 is degassed at 200° C. in vacuo and poured into a mould preheated to 200° C., of dimensions 120×120×4 mm. The mouldings are cured at 200° C. for 3 hours, at 220° C. for 3 hours and at 250° C. for 6 hours. After cooling, the sheets are cut into test bars, and the following properties are measured:

Bending strength (according to ISO 178): 132N/mm².

Outer fibre stress (according to ISO 178): 6.4%.

Tensile shear strength (according to ISO 4587): 10.5N/mm².

Glass transition temperature (TMA)[1]: 238° C.

[1] Measured using a thermoanalyzer duPont 9900

EXAMPLE B2

The bisimide prepared according to Example A6 is poured as a hot low-viscosity resin into a test tube and cured at 200° C. for 3 hours, at 220° C. for 3 hours and at 250° C. for 6 hours. This gives a clear solid which has a glass transition temperature of 251° C.

EXAMPLE B3

A mixture of 75 g of 4,4'-bis-(4-allylbicyclo[2.2.1]hept-5-ene-2,3-dicarboximidylphenoxy)diphenyl ether, prepared according to Synthesis Example A2, and 75 g of 4,4'-diphenylmethanebismaleimide is melted at 150° C. The clear melt is degassed at 180° C. for 10 minutes, then poured into a mould of dimensions 120×120×4 mm³ and cured at 180° C. for two hours, at 200° C. for one hour, at 220° C. for three hours and at 250° C. for six hours. Demoulding gives a clear red-brown transparent sheet with which the following polymer properties are measured:

Bending strength: 137N/mm²;
Outer fibre stress: 5.6%;
Glass transition temperature (TMA): >300° C.

EXAMPLE B4

A mixture of 10 g of 4,4'-bis(4-allylbicyclo[2.2.1]hept-5-ene-2,3-dicarboximidylphenoxy)diphenyl ether, prepared according to Synthesis Example A2, and 10 g of Copimide 353 (mixture of different bismaleimides; commercial product from Technochemie GmbH Verfahrenstechnik, D-6915 Dossenheim, FRG) is melted at 130° C.–150° C. The clear low-viscosity melt is then poured into a test tube and cured at 200° C. for 3 hours, at 220° C. for 3 hours and at 280° C. for 6 hours. This gives a clear bubble-free solid which has a glass transition temperature of >350° C.

EXAMPLE B5

A mixture of 10 g of 4,4'-bis(4-allylbicyclo[2.2.1]hept-5-ene-2,3-dicarboximidylphenoxy)diphenyl ether, prepared according to Synthesis Example A2, and 10 g of N,N'-4,4'-methylenebis(2-ethyl-6-methylphenylmaleimide) (prepared according to JP-A 61/93159) is melted at 150° C. The clear liquid melt is then poured into a test tube and cured as described in Example B4. This gives a clear bubble-free solid which has a glass transition temperature of >300° C.

C. PREPARATION OF THE INTERMEDIATE OF THE FORMULAE VI AND VII

EXAMPLE C1

1,4-Bis-{1-[4-(4-nitrophenoxy)phenyl]-1-methylethylidene}-benzene

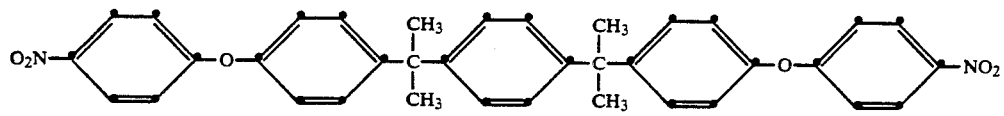

692.9 g (2.0 mol) of bisphenol P from Mitsui Petrochemical Industries Ltd., 630.3 g (4.0 mol) of 1-chloro-4-nitrobenzene and 608.2 g (4.4 mol) of anhydrous potassium carbonate in 2000 ml of dimethylformamide are reacted at 138° to 139° C. for 5 hours and 10 minutes. After the reaction is completed, the still hot reaction solution is poured into 15 liters of water with stirring, the precipitated product is filtered off with suction and washed with water, and the residue is dried at 110° C. in vacuo. This gives 1142.3 g (97% of theory) of a yellowish crystalline dinitro compound which melts at 195° C.

| | Elemental analysis: | | |
|---|---|---|---|
| | % C | % H | % N |
| calculated | 73.45 | 5.48 | 4.76 |
| found | 72.93 | 5.57 | 4.72. |

EXAMPLE C2

1,4-Bis-{1-[4-(4-aminophenoxy)phenyl]-1-methylethylidene}-benzene

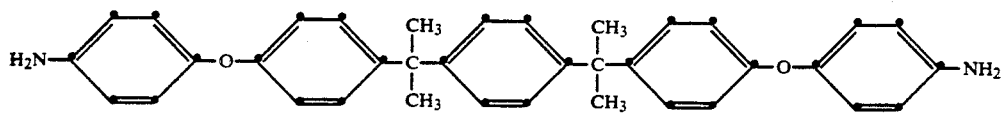

1190 g (2.02 mol) of the dinitro compound described in Example C1 are reduced at 45° C. in the presence of hydrogen (4 bar) for 1.5 hours in a suspension of 33 g of 5% Pd/carbon in 11 liters of dimethylformamide. The reaction solution is then filtered, and the product is precipitated by pouring the filtrate into 25 liters of water. The product is extracted 3 times with chloroform, the organic phases are combined, the solution is dried with anhydrous sodium sulfate and filtered, and the filtrate is concentrated at 70° C./vacuum on a rotary evaporator. The residue is dried at 120° C./0.2 mbar, until the weight remains constant, to give 907.3 g (92.7% of theory) of the desired diamine which melts at 190° C.

| | Elemental analysis: | | |
|---|---|---|---|
| | % C | % H | % N |
| calculated | 81.79 | 6.86 | 5.30 |
| found | 81.71 | 6.72 | 5.25. |

What is claimed is:

1. A compound of the formula I

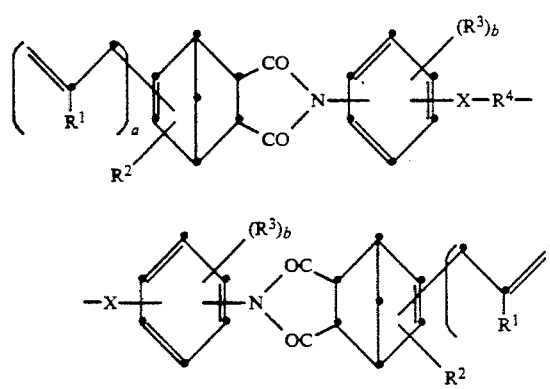

in which a is 1, 2 or 3, b is 0, 1 or 2, $R^1$ and $R^2$, independently of one another, are hydrogen or methyl, $R^3$ is $C_1-C_6$alkyl, $R^4$ is selected from the group consisting of the formulas IIa, IIb, IIc, IId, IIe or IIf

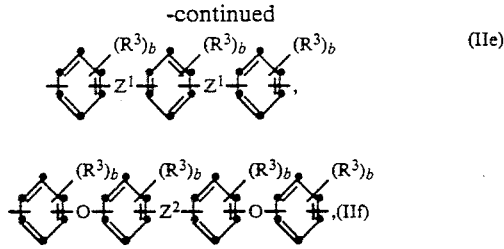

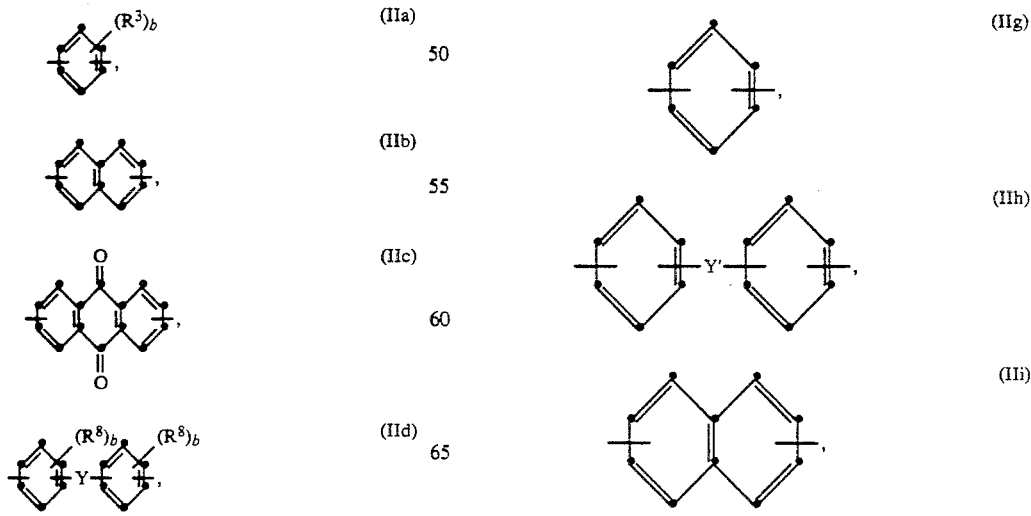

X is —O—, —S—, —CO—, —COO—, —CO—NR⁵— or —CR⁶R⁷—, $Z^1$ is —CR⁶R⁷—, $Z^2$ is —SO₂— or —CO—, Y is a direct C—C bond, —O—, —S—, —SO—, —SO₂—, —CO—, —P(O)R⁹—, —COO—, —CO—NR⁵—, —$C_nH_{2n}$— or —CR¹⁰R¹¹—, n is an integer from 1 to 12, $R^5$ is hydrogen or $C_1-C_6$alkyl, $R^6$ and $R^7$, independently of one another, are hydrogen, $C_1-C_6$alkyl, —CF₃, cyclohexyl or phenyl, or $R^6$ and $R^7$ together with the common C atom are a cycloalkylidene radical having 5 to 7 ring carbon atoms, $R^8$ is $C_1-C_6$alkyl, chlorine or bromine, $R^9$ is methyl, cyclohexyl or phenyl, $R^{10}$ is —CF₃, cyclohexyl or phenyl, $R^{11}$ can adopt one of the meanings of $R^{10}$ or is additionally hydrogen, or $R^{10}$ and $R^{11}$ together with the common C atom are a cycloalkylidene radical having 5 to 7 ring carbon atoms.

2. A compound of the formula I according to claim 1, in which a is 1, b is 0 and $R^2$ is hydrogen.

3. A compound of the formula I according to claim 1, in which $R^4$ is a group of the formula IIa, IIb or IId and b is 0.

4. A compound of the formula I according to claim 1, in which X is —C(CH₃)₂— or —O—.

5. A compound of the formula I according to claim 4, in which X is —O—.

6. A compound of the formula I according to claim 1, in which Y is a direct C—C bond, —S—, —SO₂—, —CH₂—, —C(CH₃)₂—, —CO—, —O— or —C(CF₃)₂— and in which Z is —CH₂— or —C(CH₃)₂—.

7. A compound of the formula I according to claim 6, in which Y is —O— or —C(CF₃)₂—.

8. A compound of the formula I according to claim 1, in which X is —C(CH₃)₂— or —O— and $R^4$ is selected from a group of the formulae IIg, IIh or IIi in which Y' is a direct C—C bond, —O—, —S—, —SO$_2$—, —C(CF$_3$)$_2$— or —C$_n$H$_{2n}$—, n is as defined in claim 1, the free valencies are in the 1,2-or 1,4-position with respect to one another in radical IIg, in the 1,2-or 1,4-position with respect to the corresponding bridge in radical IIh and in the 1,5-, 2,6- or 2,7-position with respect to one another in radical IIi.

9. A compound of the formula I according to claim 8, in which X is —O—.

10. A compound of the formula I according to claim 1, in which X is —O— and R$^4$ is a radical of the formula IIj

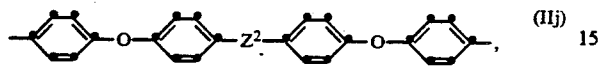

in which Z$^2$ is as defined in claim 1.

11. A compound of the formula III according to claim 1

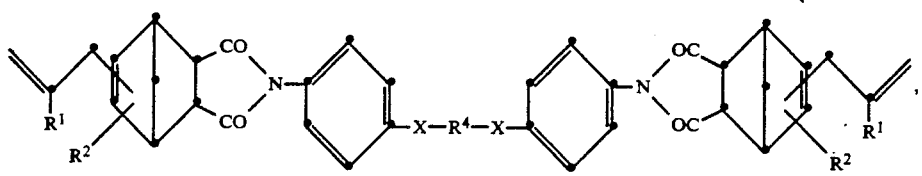

in which R$^1$, R$^2$, R$^4$ and X are as defined in claim 1.

12. A compound of the formula IIIa according to claim 11

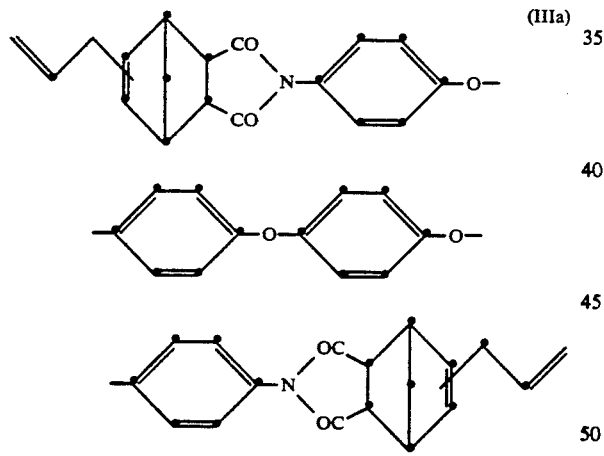

13. A composition containing

A) at least one compound of the formula I according to claim 1 and
B) at least one compound of the formulae VIII or IX

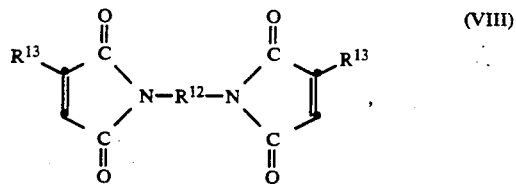

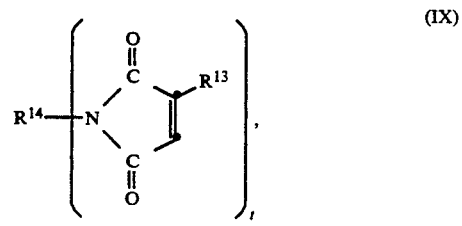

in which t is an integer from 3 to 12, R$^{12}$ is alkylene, cycloalkylene, arylene, aralkylene or a divalent heterocyclic radical containing one or two N, O or S atoms, R$^{13}$ is methyl or hydrogen and R$^{14}$ is a t-valent radical of an aromatic polyamine after the removal of t amino groups.

14. A composition according to claim 13, in which R$^{13}$ is hydrogen.

15. A composition according to claim 13, in which R$^{12}$ is a radical of the formulae IIa or IId according to claim 1 and R$^{13}$ is hydrogen.

16. A composition according to claim 13 which contains as a component A), a compound of the formula I according to claim 1 in which a is 1, b is 0, X is —O— and R$^4$ is a radical of the formula IId according to claim 1 in which Y is —O— and which contains, as a component B), a compound of the formula VIII according to claim 12 in which R$^{13}$ is hydrogen and R$^{12}$ is a binuclear aromatic radical whose nuclei are linked via a bridging group.

17. A compound of the formulae VIa, VIb, VIc and VId

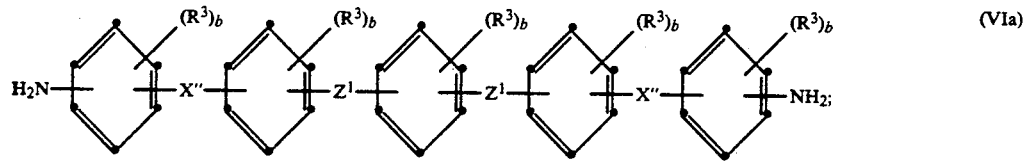

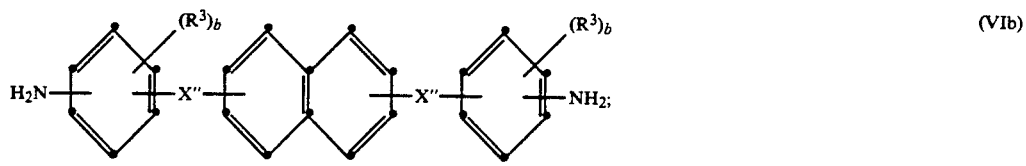

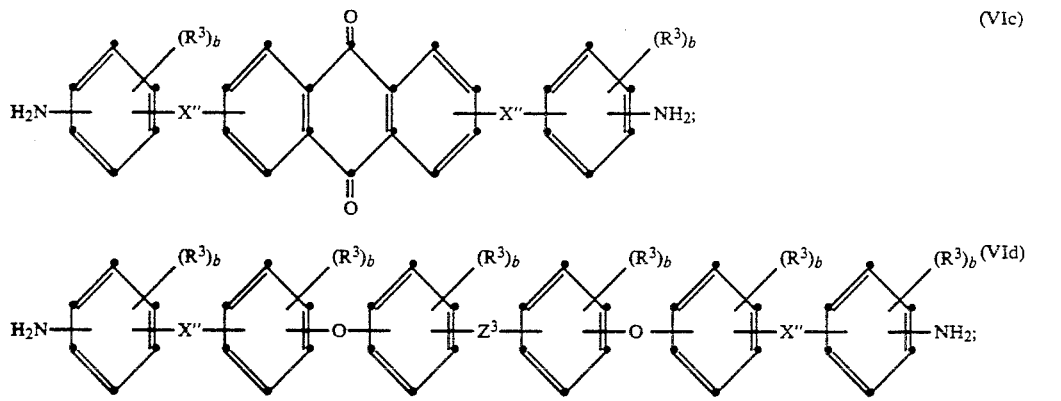
in which $R^3$, $Z^1$ and b are as defined in claim 1, X" is —O—, —S—, —CO— or —COO— and $Z^3$ is —CO—.
18. A compound of the formulae VIIa, VIIb, VIIc and VIId
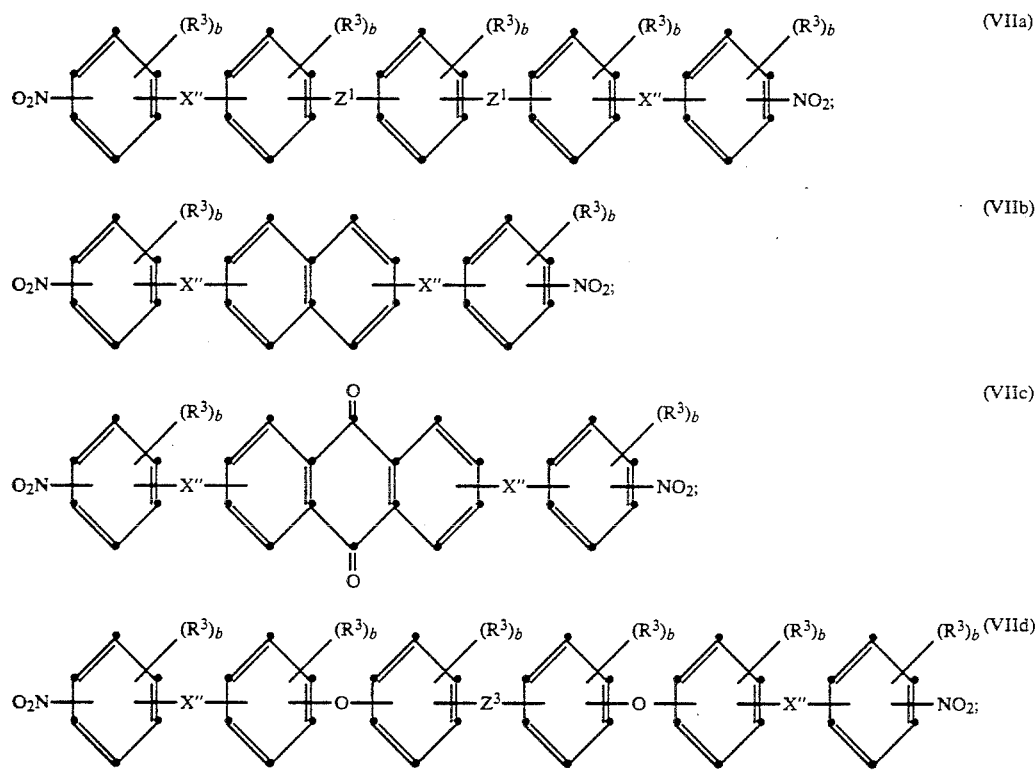
in which $R^3$, $Z^1$ and b are as defined in claim 1 and X" and $Z^3$ are as defined in claim 17.